United States Patent
Toro Casasnovas

(10) Patent No.: US 10,973,945 B2
(45) Date of Patent: Apr. 13, 2021

(54) FREEZER FOR BIOSANITARY AND CYTOTOXIC WASTE

(71) Applicant: BIOSEGURIDAD SANITARIA POR FRIO, S. L., Madrid (ES)

(72) Inventor: Eduardo Toro Casasnovas, Madrid (ES)

(73) Assignee: BIOSEGURIDAD SANITARIA POR FRIO, S. L., Madrid (ES)

( * ) Notice: Subject to any disclaimer, the term of this patent is extended or adjusted under 35 U.S.C. 154(b) by 281 days.

(21) Appl. No.: 16/094,948

(22) PCT Filed: Apr. 29, 2016

(86) PCT No.: PCT/ES2016/070330
§ 371 (c)(1),
(2) Date: Oct. 19, 2018

(87) PCT Pub. No.: WO2017/186977
PCT Pub. Date: Nov. 2, 2017

(65) Prior Publication Data
US 2019/0125918 A1 May 2, 2019

(51) Int. Cl.
*A61L 9/20* (2006.01)
*B01D 53/88* (2006.01)
(Continued)

(52) U.S. Cl.
CPC .............. *A61L 9/205* (2013.01); *A61L 9/20* (2013.01); *B01D 53/007* (2013.01); *B01D 53/885* (2013.01); *B01J 21/063* (2013.01); *B01J 35/004* (2013.01); *B65F 1/1426* (2013.01); *B65F 1/163* (2013.01); *B65F 7/00* (2013.01);
(Continued)

(58) Field of Classification Search
None
See application file for complete search history.

(56) References Cited

U.S. PATENT DOCUMENTS 3,322,477 A * 5/1967 Armijo ................ B65F 1/1607
312/211
4,592,192 A 6/1986 Jacob et al.
(Continued)

FOREIGN PATENT DOCUMENTS

CN 105465898 A 4/2016
ES 1062531 U * 7/2006
(Continued)

OTHER PUBLICATIONS

English machine translation for ES 1062531 U (Jul. 2006). Retrieved from EPO website on Mar. 24, 2020. (Year: 2020).*

*Primary Examiner* — Jennifer A Leung
(74) *Attorney, Agent, or Firm* — Banner & Witcoff, Ltd.

(57) ABSTRACT

Freezer for biosanitary and cytotoxic waste, which comprises an inner space that houses a waste container, a front door through which the waste container in the inner space is inserted/removed, an upper door through which waste is poured into the inner container, cooling means and inner space temperature control means, wherein, the freezer further comprises an air purifier that treats an air stream coming from the inner space, when opening one of its doors, thus avoiding the emission of both chemical and biological particulate contaminants to the outside environment.

12 Claims, 1 Drawing Sheet

(51) Int. Cl.
- *B65F 1/14* (2006.01)
- *B65F 1/16* (2006.01)
- *F25D 11/00* (2006.01)
- *B65F 7/00* (2006.01)
- *B01D 53/00* (2006.01)
- *B01J 21/06* (2006.01)
- *B01J 35/00* (2006.01)

(52) U.S. Cl.
CPC ........... *F25D 11/00* (2013.01); *A61L 2209/10* (2013.01); *A61L 2209/12* (2013.01); *B01D 2255/20707* (2013.01); *B01D 2255/802* (2013.01); *B01D 2259/804* (2013.01); *B65F 2210/116* (2013.01)

(56) References Cited

U.S. PATENT DOCUMENTS

| | | |
|---|---|---|
| 5,908,601 A | 6/1999 | Lin |
| 2013/0129565 A1* | 5/2013 | Siaw .................... B01D 53/885 422/4 |

FOREIGN PATENT DOCUMENTS

| | | | |
|---|---|---|---|
| ES | 1069670 U | * | 4/2009 |
| ES | 1209438 U | * | 4/2018 |
| FR | 2724915 A1 | | 3/1996 |

* cited by examiner

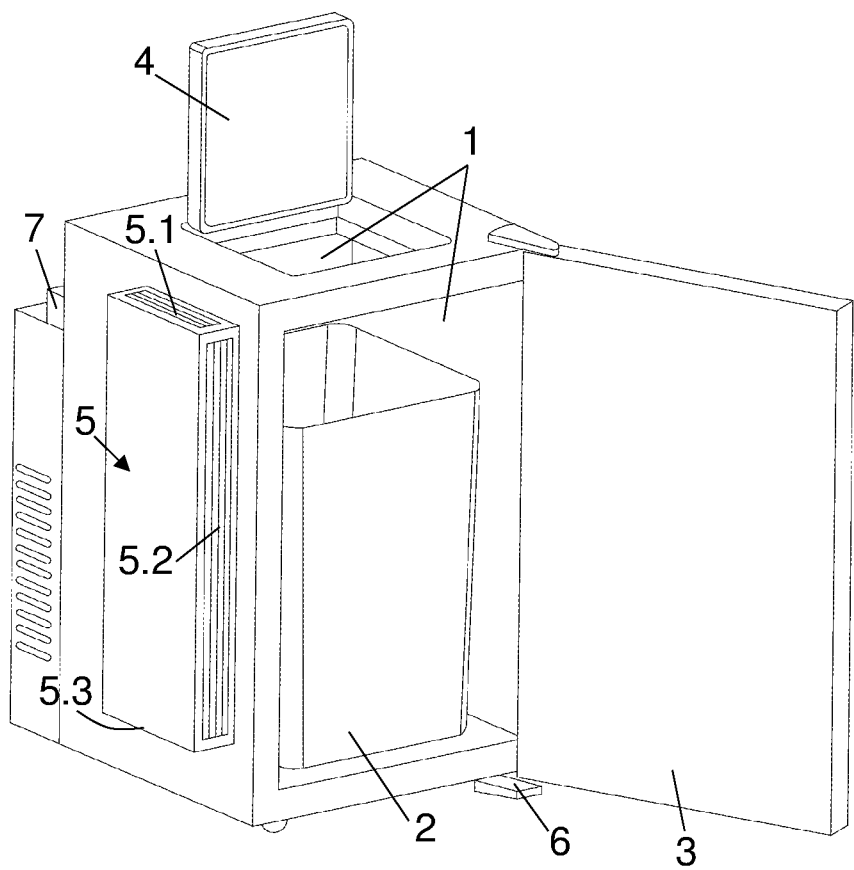

FREEZER FOR BIOSANITARY AND CYTOTOXIC WASTE

The present application is a U.S. National Phase Application under 35 U.S.C. § 371 of PCT/ES2016/070330 filed Apr. 29, 2016 which is incorporated by reference herein in its entirety.

FIELD OF THE INVENTION

The object of the present invention is a freezer for biosanitary and cytotoxic waste of the type used in hospitals, or for the transportation of such waste to incineration plants, using refrigeration means that are able to delay the degradation of such waste; incorporating as a novelty, an air purifier by titanium dioxide photocatalysis to cancel out the emissions of particulate contaminants produced by the waste contained in its interior.

BACKGROUND OF THE INVENTION

Different designs of refrigerators for biosanitary and cytotoxic waste are known. For example, the one shown in Spanish utility model ES 1062531 U, published on 1 Jul. 2006, which comprises a front door that allows insertion and removal of a container where the waste is deposited, an upper door to pour the waste into the container. The refrigerator has respective coils arranged on the side walls and rear wall, as well as a thermostat that regulates the temperature inside the refrigerator.

These known refrigerators have the disadvantage that, when opening either the upper door or the front door, both chemical and biological particulate contaminants are emitted to the outside environment together with the air stream coming from the interior of the refrigerator.

For this reason, a freezer for biosanitary and cytotoxic waste needs to be designed, which is able to simply and economically solve the disadvantage of the aforementioned prior art.

DESCRIPTION OF THE INVENTION

The present invention is established and characterised in the independent claims, while the dependent claims describe additional features thereof.

The object of the invention is a freezer for biosanitary and cytotoxic waste. The technical problem to solve is how to prevent the emission of particulate contaminants to the outside environment, when opening a door of the freezer.

An advantage of the invention is that it manages to effectively provide a solution to the technical problem addressed, as the arrangement of the air purifier at the outlet of the freezer door, enables treatment of the stream of air coming from the inner space of the freezer when any of its doors has been opened, thus avoiding the emission of both chemical and biological particulate contaminants to the outside environment.

BRIEF DESCRIPTION OF THE FIGURES

This specification is complemented with a FIGURE that illustrates the preferred example of the invention, in no way intended to limit the scope thereof.

FIG. 1 shows a perspective view of the freezer for biosanitary and cytotoxic waste.

DETAILED DESCRIPTION OF THE PREFERRED EMBODIMENT OF THE INVENTION

This invention is a freezer for biosanitary and cytotoxic waste.

As shown in FIG. 1, the freezer comprises:
an inner space (1), which houses a waste container (2),
a front door (3), through which the waste container (2) in the inner space (1) is inserted/removed,
an upper door (4), through which the waste is poured into the inner container (2),
cooling means (7) and temperature control means (not shown in the FIGURE) of the inner space (1).

For example, the cooling means (7) may comprise respective coils (not shown in the FIGURE) arranged on the side walls and rear wall of the freezer; and, the temperature control means may be a thermostat (not shown in the FIGURE) that regulates the temperature in the inner space (1) of the freezer between 0° C. and −25° C.

Likewise, the freezer comprises an air purifier (5) that treats an air stream coming from the inner space (1). The air purifier (5) may be arranged on the outside of the freezer, for example, on one of its sides.

Preferably, the air purifiers (5) comprises an upper air inlet (5.1), oriented towards the upper door (4); similarly, it may comprise a front air inlet (5.2), oriented towards the front door (3) of the freezer.

Likewise, it is preferred that the air purifier (5) is put into operation when opening the upper door (4) or the front door (3). Being preferred that the upper door (4) or the front door (3) open by operating an accessible pedal (6), either at the front of the freezer or at one of its sides.

The air purifier (5) may comprise impeller means, for example, a fan (not shown in FIGURE), that drag the air stream coming from the inner space (1) towards the air purifier (5), when the upper door (4) or front door (3) of the freezer is opened. At the same time, such impeller means transfer the air stream with particulate contaminants through the interior of the air purifier (5), between the upper air inlets (5.1) or front air inlets (5.2), and a purified air outlet (5.3).

On the other hand, it is preferred that the air stream coming from the inner space (1) is treated in the air purifier (5) by photocatalysis, for example, using titanium dioxide ($TiO_2$) as photo-catalyst. For this purpose, the air purifier (5) may comprise in its interior a matrix of titanium dioxide ($TiO_2$) (not shown in the FIGURE) irradiated by ultraviolet (UV) lamps (not shown in the FIGURE). The air stream transferred between the inlets (5.1, 5.2) and the outlet (5.3) of the air purifier (5) flows through the irradiated matrix.

In passing through the air purifier (5), the air stream with particulate contaminants, coming from the inner space (1) of the freezer, is converted into purified air at the outlet of the air purifier (5), cancelling out the emission to the outside environment of both chemical and biological particulate contaminants, which come from the biosanitary and cytotoxic waste in segregation phase contained in the container (2) of the inner space (1) of the freezer.

The cleaning of the air stream occurs when the accompanying particulate contaminants "oxidise" by contact with the hydroxyl radicals and superoxide ions formed when the titanium dioxide ($TiO_2$) absorbs the photons coming from the ultraviolet (UV) lamps, until managing to completely reduce these particulate contaminants to carbon dioxide ($CO_2$) and water vapour; obtaining as a result purified air suitable to be emitted to the outside environment, without risk of contamination thereof.

The invention claimed is:

1. A freezer for biosanitary and cytotoxic waste, comprising:
   an inner space, which houses a waste container,
   a front door configured to swing on a vertical axis away from the inner space, through which the waste container in the inner space is inserted or removed therefrom,
   an upper door configured to swing away from the inner space on a horizontal axis, through which waste is poured into the waste container when the upper door is opened,
   a cooling means,
   an inner space temperature control means, and
   an air purifier that simultaneously treats air streams coming from the inner space and air surrounding the freezer,
   wherein the air purifier is mounted on an exterior sidewall of the freezer, the air purifier having a housing comprising a horizontal upper air inlet and a vertical front air inlet and a purified air outlet disposed laterally opposite of the horizontal upper air inlet, wherein, the upper air inlet is oriented towards the upper door and arranged to draw an upper air stream from the inner space by way of the upper door being opened and the front air inlet is oriented towards the front door and arranged to draw a front air stream from the inner space by way of the front door being opened; wherein the upper air stream and the front air stream are collectively transferred within an interior of the housing to the purified air outlet such that treated purified air is discharged underneath the housing.

2. The freezer according to claim 1, wherein the exterior sidewall on which the air purifier is mounted is a left sidewall on the outside of the freezer, when a user is facing the front door.

3. The freezer according to claim 1, wherein the air purifier is put into operation when opening the upper door or the front door.

4. The freezer according to claim 1, wherein the upper door or the front door is open by operating a pedal.

5. The freezer according to claim 1, wherein the air purifier treats the air streams coming from the inner space by photocatalysis.

6. The freezer according to claim 5, wherein the photocatalyst used in the photocatalysis is titanium dioxide ($TiO_2$).

7. The freezer according to claim 6, wherein the air purifier comprises a matrix of titanium dioxide ($TiO_2$) irradiated by ultraviolet (UV) lamps.

8. The freezer according to claim 1, wherein the air purifier comprises an air stream impeller means.

9. A freezer for biosanitary and cytotoxic waste, comprising:
   an inner space;
   a temperature control device configured to regulate a temperature of the inner space between 0° C. to −25° C.;
   a front door configured to pivot on a vertical axis away from the inner space;
   an upper door configured to pivot away from the inner space on a horizontal axis; and
   an air purifier being mounted on an exterior sidewall of the freezer;
   wherein the air purifier includes a housing having a horizontal upper air inlet, a vertical front air inlet, and a purified air discharge outlet disposed laterally opposite of the horizontal upper air inlet; wherein the upper air inlet is disposed towards the upper door and arranged to draw an upper air stream from the inner space when the upper door is in an opened position, and the front air inlet is disposed towards the front door and arranged to draw a front air stream from the inner space when the front door is in an opened position; wherein the upper air stream and the front air stream are collectively transferred within an interior of the housing to an interior matrix of titanium dioxide and UV lamps configured to treat chemical and biological particulate contaminants emanating from the inner space to a carbon dioxide and water vapor mixture so as to discharge the mixture through the purified air discharge outlet underneath the air purifier.

10. The freezer according to claim 9, further comprising a waste container configured to be received in the inner space.

11. The freezer according to claim 9, wherein the air purifier comprises air stream impeller.

12. The freezer according to claim 9, wherein the exterior sidewall on which the air purifier is mounted is located opposite of the vertical axis on which the front door pivots.

* * * * *